(12) United States Patent
Artzi et al.

(10) Patent No.: US 9,480,404 B2
(45) Date of Patent: Nov. 1, 2016

(54) METHOD FOR IMAGING BIOMATERIAL EROSION IN VIVO

(75) Inventors: Natalie Artzi, Brookline, MA (US); Elazer R. Edelman, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1073 days.

(21) Appl. No.: 12/578,365

(22) Filed: Oct. 13, 2009

(65) Prior Publication Data

US 2011/0085712 A1   Apr. 14, 2011

Related U.S. Application Data

(60) Provisional application No. 61/104,346, filed on Oct. 10, 2008.

(51) Int. Cl.
*G06K 9/00*   (2006.01)
*A61B 5/00*   (2006.01)
*G06F 19/00*   (2011.01)
*G06T 7/00*   (2006.01)

(52) U.S. Cl.
CPC ........... *A61B 5/0059* (2013.01); *G06F 19/321* (2013.01); *G06T 7/0012* (2013.01)

(58) Field of Classification Search
CPC .......... G06T 2207/10072; G06T 2207/10101; G06T 2207/20148; G06T 2207/30021; G06T 2207/30048; G06T 2207/30101; G06T 2207/30242; G06T 7/0012; G06T 7/0051; G06T 7/0081; G06T 7/60
USPC ....................................................... 382/128
See application file for complete search history.

(56) References Cited

U.S. PATENT DOCUMENTS

| | | | |
|---|---|---|---|
| 6,775,567 B2 | 8/2004 | Cable et al. | |
| 2002/0077677 A1* | 6/2002 | Beck et al. | ................... 607/88 |
| 2004/0081692 A1* | 4/2004 | Sharma | ............... G06F 19/704 424/468 |
| 2004/0201756 A1* | 10/2004 | VanBree | .................... 348/239 |
| 2005/0013793 A1* | 1/2005 | Beckman | ............ C08G 18/12 424/78.27 |
| 2008/0031507 A1* | 2/2008 | Uppaluri et al. | ............. 382/132 |
| 2010/0219353 A1* | 9/2010 | Akiyoshi | .......... G02B 21/0088 250/459.1 |
| 2016/0078309 A1* | 3/2016 | Feldman | ............. G01B 9/0203 382/131 |

OTHER PUBLICATIONS

Yang, et al., On-Line Fluorescent Monitoring of the Degradation of Polymeric Scaffolds for Tissue Engineering, Analyst, 2005, 130:1502-1506.

* cited by examiner

*Primary Examiner* — Reginald R Reyes
(74) *Attorney, Agent, or Firm* — Quarles & Brady LLP

(57) ABSTRACT

A method for imaging the erosion of a biomaterial is disclosed. More specifically, the present invention provides a method for imaging a labeled biomaterial so that the erosion of the biomaterial is measured in vivo over a period of time. A biomaterial such as, for example, a hydrogel including polyethylene glycol (PEG) is labeled with a fluorescent or bioluminescent marker. The labeled biomaterial is then employed in the construction of an implanted medical device such as, for example, an endovascular stent. Furthermore, the labeled biomaterial may be utilized to form a drug delivery system that releases a controlled amount of a drug into a local region within a patient. The erosion of the biomaterial is monitored through a noninvasive imaging method.

16 Claims, 4 Drawing Sheets

METHOD FOR IMAGING BIOMATERIAL EROSION IN VIVO

CROSS-REFERENCE TO RELATED APPLICATIONS

This application is based on, claims the benefit of, and incorporates by reference U.S. Provisional Application Ser. No. 61/104,346 filed Oct. 10, 2008, and entitled "Method For Imaging Biomaterial Erosion In Vivo."

BACKGROUND OF THE INVENTION

The field of the invention is spectroscopy and, more particularly, systems for and method of spectroscopy for imaging erosion of biomaterials.

Biologically compatible and degradable materials have found an increased presence in clinical applications in recent years. Degradable biomaterials are less prone to complications associated with the long-term residence of foreign objects within a subject and can, for example, serve as platforms for structural stabilization, void filling, and tissue engineering. Beyond their use in implants and medical devices, degradable biomaterials are particularly valuable in drug delivery systems. Drugs are traditionally administered to a patient via injection or oral delivery, for example, using pills. These drug administration methods generally involve high drug concentrations that can lead to adverse side effects. To reduce complications associated with high drug concentrations, biomaterials such as biodegradable hydrogels can be employed to target drug delivery to a local region and provide controlled drug release over an extended time period. Hydrogel drug delivery systems, for example, can be employed to deliver pharmaceutical compounds including hormones, enzymes, antibiotics, and even cell suspensions. Also, endovascular stents may sometimes be coated with a polymer that releases a pharmaceutical to control restenosis of the vasculature. In such an application, it is often beneficial to promote endothelialization while controlling restenotic processes such as platelet aggregation and smooth muscle cell proliferation. Therefore, accurate characterization of in vivo biomaterial erosion, and its relationship to drug diffusion rates, is beneficial for the development of drug delivery systems that provide appropriate drug efflux to a region within a patient.

Biomaterial erosion can be followed in vitro using a number of techniques, most of which are inferential. Periodic sampling of biomaterial weight has traditionally served as a primary measure of erosion. However, this assumes that biomaterial weight change is strictly due to erosion and fails to account for biomaterial swelling, for example, due to solvent influx. Biomaterial swelling typically occurs in a non-linear fashion that is determined not only by solute properties, but by environmental conditions as well. Swelling of a biomaterial due to water uptake can continue for up to four days and peak swelling is typically followed by a period of rapid erosion and weight change. Because they produce different byproducts, different biomaterials can have a wide range effects on their local environment. Local environmental conditions, such as pH and local strain, can in turn affect biomaterial swelling and mass change occur. Since weight gain is often observable for a substantial period before weight loss, it can mask weight changes due to biomaterial erosion. Therefore, mass change cannot be relied upon as a sensitive marker of biomaterial erosion, especially when the biomaterial is placed within a subject whose in vivo environment is not as directly observable compared to an in vitro environment.

Methods for measuring biomaterial erosion in vitro using fluorescence spectroscopy have been proposed. For example, in a method described by Y. Yang, et al. ("On-line Fluorescent Monitoring of the Degradation of Polymeric Scaffolds for Tissue Engineering," Analyst, 2005; (130): 1502-1506), a fluorescent dye is attached to mesoporous silica particles, or "meso-particles." Following fluorescent labeling, the meso-particles are mixed in a 5% polymer solution. As a result, the meso-particles become suspended in the polymeric biomaterial. The fluorescent intensity of the resultant biomaterial is then observed in an in vitro environment over a period of time in order to provide an indication of biomaterial erosion. However, the meso-particles disperse into the surrounding environment as the biomaterial degrades, thus reducing the efficacy of the measurements.

Loss of material integrity, structure, and eventually mass follow one another, but at different rates in the in vitro and in vivo domains. This is largely due to the complex interactions between an implanted biomaterial and its local environment. Some environmental conditions such as buffer type, buffer volume, pH, temperature, flow, and stresses can be approximated in vitro but do not necessarily represent the in vivo state. Other in vivo conditions, such as those associated with active inflammation, encapsulation, and similar reactions, cannot be recapitulated in vitro. Moreover, in vitro degradation analysis by traditional techniques often fails to distinguish between erosion, absorption, and degradation and does not always provide an accurate indication of in vivo performance, particularly when the biomaterials are formed into complex, three-dimensional structures. Accordingly, the utility of many degradable biomaterials for complex, implantable structures is severely limited when their behavior in vivo does not followed expectations based upon observed in vitro biodegradation kinetics. This mismatch between domains is illustrated by recent problems with bioerodible vascular stents. Traditional metal stents coated with permanent polymeric materials can have problems associated with long-term biocompatibility. It was hoped that bioerodible stents could provide a less problematic alternative. In clinical trials, however, bioerodible stents exhibited slower degradation and reduced biocompatibility than expected based upon extensive in vitro characterization and animal model examination. While they ultimately degrade, the stents' slow erosion necessitates long-term patient follow-up before it can be determined that the device is safe and stable. This behavior has strong regulatory implications and ultimately leads to the cancellation of the clinical trials.

Biomaterial degradation in vivo can be measured by tracking critical metabolites or byproduct appearance. For example, polyaminoacid breakdown can be followed by the appearance of amino acids. The reliability of such methods is based on the tenuous assumption that the appearance of byproducts, clearance in media, and analytic resolution are unaffected by the degradation of the biomaterial. Moreover, methods of mass or biochemical assay do not adequately account for the structural configuration of the biomaterial. Accordingly, blocks, drops, gels, and reticular networks of biomaterials of equal mass will typically degrade with significantly different kinetics.

Other methods for measuring biomaterial erosion in vivo employ the sequential examination of implanted candidate biomaterials in a group of animals. The animals are sacrificed at different points in time and biomaterial residues are detected and measured. One of the drawbacks of this method is that the implantation of a biomaterial in an animal is rarely indicative of the expected clinical application. Moreover, the detection of erosion is most often crude and mechanical rather than mechanistic. While these methods require the use of large numbers of animals, they estimate of the extent of biomaterial erosion and do not track factors such as biomaterial secretion and biomaterial migration from the implantation site.

The limitations of traditional in vivo biomaterial erosion measurements and the inability to properly relate biomaterial fate between the in vitro and in vivo domains significantly limits the utility of many biomaterials. It would therefore be desirable to have a noninvasive method for tracking biomaterial erosion in vivo.

SUMMARY OF THE INVENTION

The present invention overcomes the aforementioned drawbacks by providing a non-invasive method for imaging biomaterial erosion in vivo. The method includes preparing an in vivo biomaterial sample by tagging a sample of the biomaterial with a marker that bonds to the biomaterial, introducing the tagged biomaterial sample to an in vivo environment, and acquiring imaging data from the in vivo environment including the tagged sample of the biomaterial over a selected time period. The method further includes reconstructing a series of images form the imaging data, each image characterizing a luminescent property of the in vitro biomaterial sample at a given time in the selected time period, determining, from the images, changes in the luminescent property of the biomaterial sample the selected time period, and correlating the changes in the luminescent property of the biomaterial sample to an in vivo marker decay characteristic indicative of the erosion of the biomaterial in vivo.

This present invention can thus be employed to analyze in vitro biomaterial samples and generate a model relating erosion in the in vivo and in vitro domains. The model enables the prediction of biomaterial performance based on observed in vitro erosion. By including additional luminescent markers, the method can also track drug delivery and viability of embedded cells with biomaterial erosion and determine the mode of degradation.

Various other features of the present invention will be made apparent from the following detailed description and the drawings.

DETAILED DESCRIPTION OF THE PREFERRED EMBODIMENT

The present invention, in part, is directed to a method for non-invasively tracking biomaterial erosion in vivo. This information can then be employed in a model relating the erosion of a given biomaterial in the in vitro and in vivo domains, which can in turn in turn be used to predict the in vivo performance of different devices utilizing the biomaterial based on their observed in vitro characteristics. Generally, this involves measuring the luminescence, for example, bioluminescence or fluorescence, of a marker attached to a biomaterial sample under study.

Figure 1:
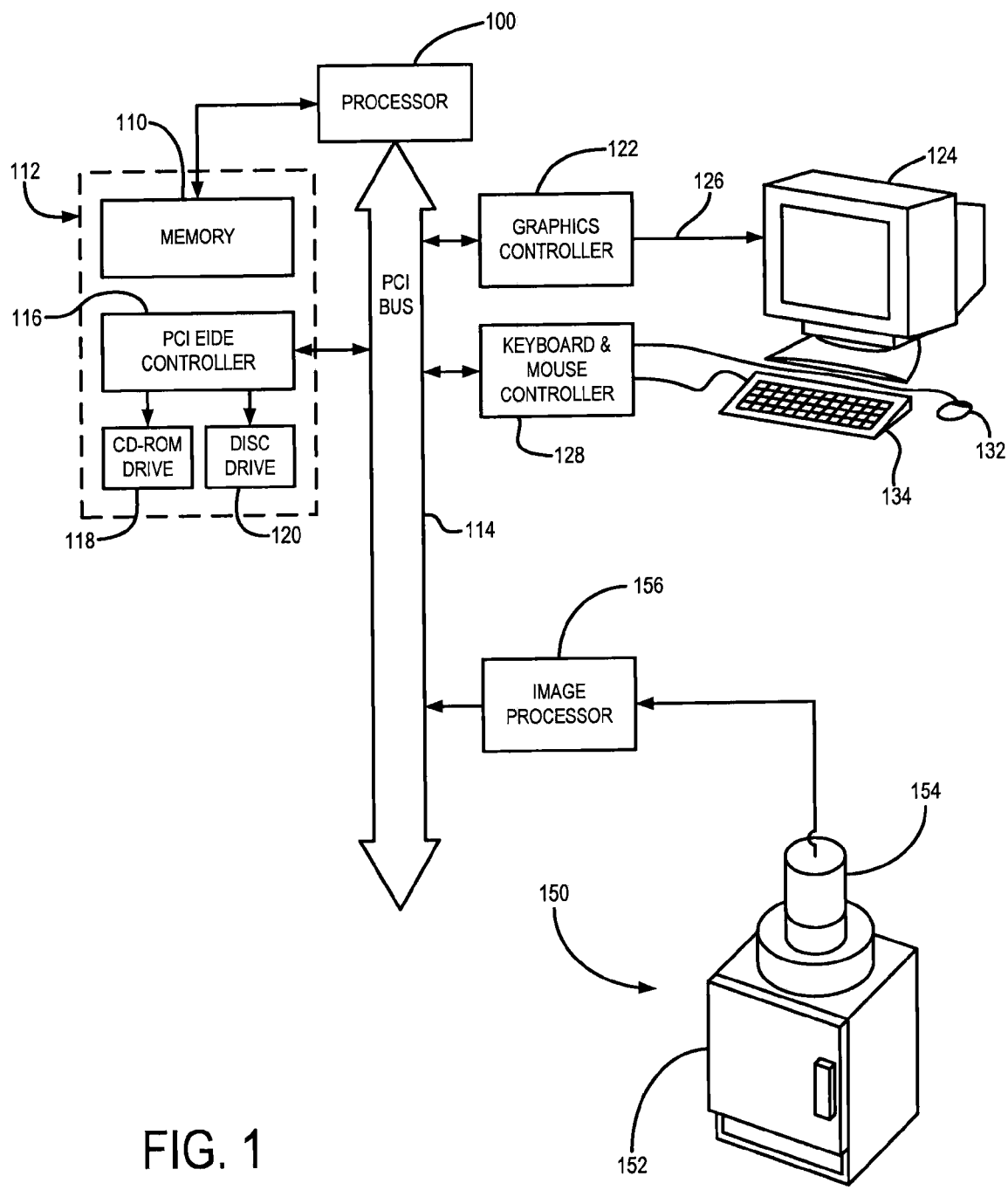
FIG. 1 is a block diagram of a system in accordance with the present invention.

An exemplary imaging system for producing images indicative of marker luminescence is shown in FIG. 1. The imaging system includes a computer workstation with a processor 100 that executes program instructions stored in a memory 110, which forms part of a storage system 112. The processor 100 is a commercially available device designed to operate with commercially available operating systems. The system includes internal memory and I/O control to facilitate system integration and integral memory management circuitry for handling all external memory 110. The system also includes a bus driver which provides a direct interface with a communications bus 114.

The communications bus 114 is an industry standard bus that transfers data between the processor 100 and a number of peripheral controller cards. These include a controller 116 that provides a high-speed transfer of data to and from, for example, an optical drive 118 and a disc drive 120. A graphics controller 122 couples the communications bus 114 to a display 124 through a standard display connection 126, and a keyboard and a mouse controller 128 receives data that is manually input through a keyboard 130 and mouse 132. For example, the display 124 may be a monitor, which presents an image measurement graphical user interface (GUI) that allows a user to view imaging results and also acts an interface to control a luminescence imaging system 150. The communications bus 114 also connects to a communications controller 140. The controller 140 connects to an intranet that links the workstation to one or more imaging systems, a department picture archiving and communication system (PACS), or an institution image management system.

The workstation controls a luminescence imaging system 150 that produces images indicative of marker luminescence, such as fluorescence from a fluorophore or bioluminescence from luciferase-expressing cells. The imaging system 150 includes a container 152 in which a biomaterial sample is placed so that low intensity luminescence can be detected. A high sensitivity camera 154, such as a charge-coupled device (CCD) camera, is placed in optical connection with the top of the container 152 so that the camera 154 is able to acquire luminescent image data from a biomaterial sample placed within the container 152. An image processor 156 interfaces between the camera 154 and the workstation via the communications bus 114, through which the workstation controls the camera 154, including motors responsible for focusing the camera 154 and motors responsible for properly positioning a platform within the container 152 that supports the biomaterial sample.

Marker luminescence can also be tracked using an in vitro imaging system (IVIS), such as is commercially available from Xenogen of Alameda, Calif., which is able to quantitatively detect fluorescent and bioluminescent signals, such as described in U.S. Pat. No. 6,775,567.

Figure 2:
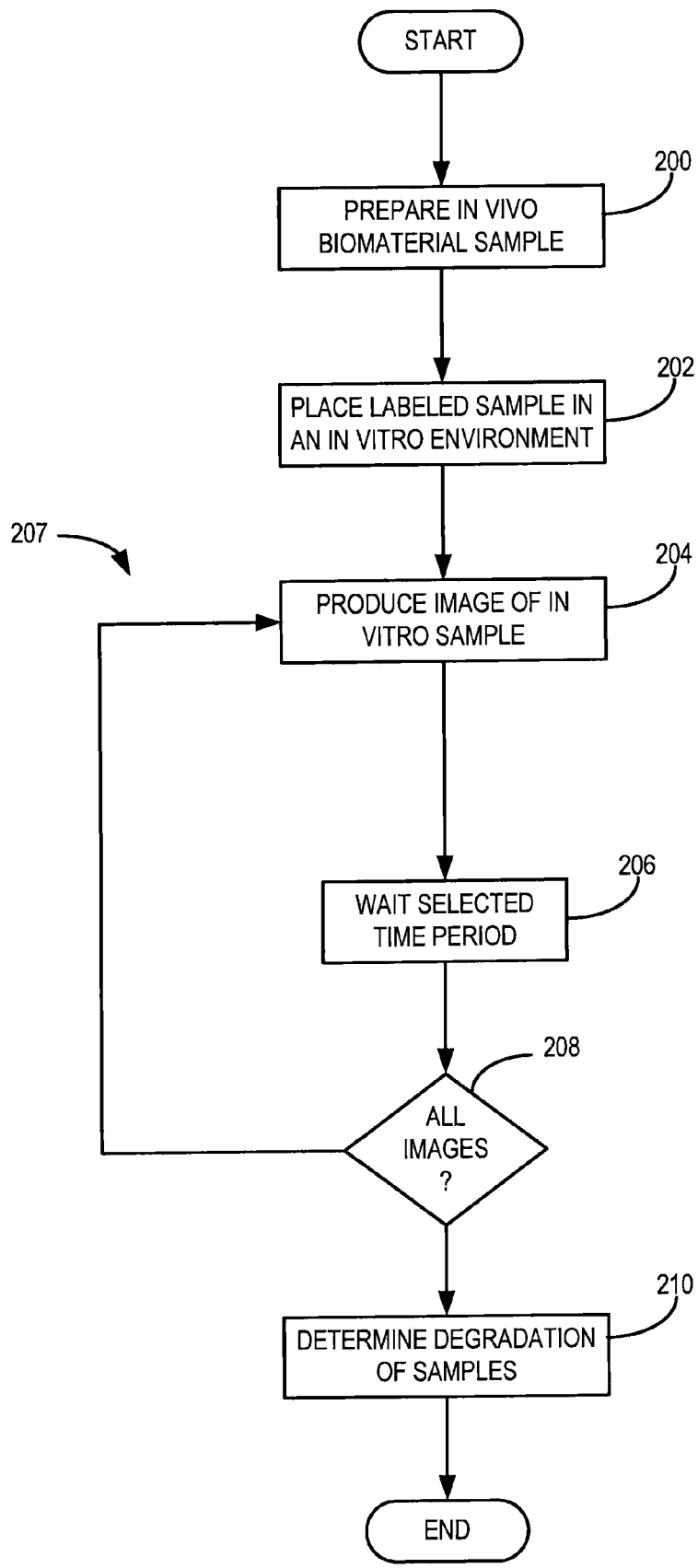
FIG. 2 is a flowchart setting forth the steps for imaging biomaterial erosion in vivo in accordance with the present invention.

Referring now to FIG. 2, the above-described imaging systems can be employed to track the erosion of a biomaterial in vivo. A method for tracking biomaterial erosion in vivo begins at process block 200 when biomaterial sample is labeled with a luminescent marker, such as a fluorophore or bioluminescent material. For example, the biomaterial sample may be polymer-based. It is contemplated that in some configurations the marker covalently bonds directly to a component of the biomaterial sample and not to an intermediate material such as a microsphere. In addition, the marker is not specific to any biomaterial, can produce light in either the visible or non-visible spectrum, is readily detectable, can be refined independently of the biomaterial, and can be used in either in vivo or in vitro environments without quenching or producing image artifacts. Biomaterial samples containing cells can be labeled using genetically-engineered luciferase, which produces bioluminescence in presence of luciferin. At process block 202, the labeled sample is introduced to a selected in vivo environment and imaged at process block 204 to produce an image indicative of sample luminescence. A selected time period is allowed to elapse, as indicated at process block 206, before an additional image of the biomaterial sample is acquired, again at process block 204. This image acquisition cycle continues, as indicated generally by the loop 207, until, at decision block 208, it is determined that a sufficient number of images have been acquired over a designated time span.

At process block 210, changes in sample luminescence between the acquired images are analyzed to determine an in vivo marker decay characteristic. For example, this can be achieved by designating a region-of-interest (ROI) around the in vitro biomaterial sample in the acquired images, which are co-registered so that the ROI is aligned with respect to the biomaterial samples throughout the image series. The in vivo marker decay characteristic are calculated by integrating the luminescence signal within the ROI for each image and analyzing changes in the resulting values between the images. For example, if analyzing a fluorophore-labeled biomaterial, the imaging system may evaluate efficiency, which is a dimensionless measure that represents the fraction of fluorescent photons relative to each incident excitation photon. Determination of the marker decay characteristic, which indicates luminescent signal decay, is beneficial because the biomaterial sample releases its luminescent markers to the surrounding environment as it degrades, thereby causing the luminescent signal within the ROI to decay over time. By assuming that luminescent signal decay is proportional to mass loss, the marker decay characteristic can serve as measure of biomaterial erosion and can be translated to quantify mass loss.

Figure 3:
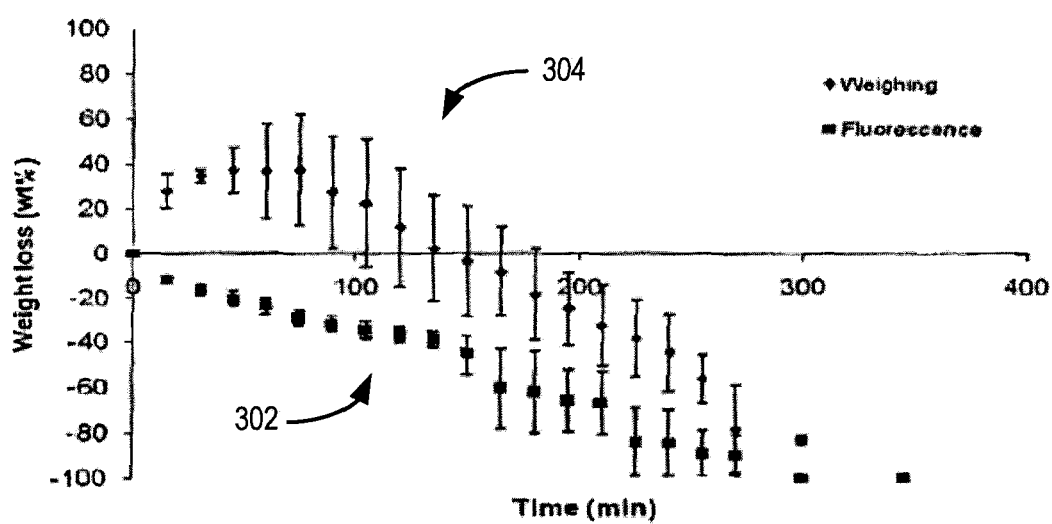
FIG. 3 is a graph comparing weighing-based biomaterial erosion to luminescence-based tracking in accordance with the present invention.

Referring now to FIG. 3, since the marker decay characteristic is not based on direct determinations of weight, it is relatively insusceptible to interference from swelling, where mass gain from water uptake masks erosion. For example, FIG. 3 compares the erosion kinetics of a fluorescently labeled PEG-dextran composition as determined by fluorescence decay tracking and conventional weighing, as indicated at 302 and 304, respectively. Fluorescence decay tracking shows increased sensitivity at early stages of erosion and significantly reduced data variance. In contrast, the data acquired via conventional weighing exhibits higher variance and fails to show initial erosion, which is masked by mass gain due to swelling. FIG. 3 also shows that the biomaterial undergoes multiphasic erosion, first by hydrolytic surface erosion and then by bulk erosion, which is more mechanically significant. Improved characterization of in vivo biomaterial erosion enables tracking of the chemical pathways involved in erosion, determination of the processes dominating erosion, and investigation of the role of biomaterial ultrastructure in the in vivo domain. Improved understanding of these factors also allows the development of more realistic in vitro environments that better approximate in vivo conditions. Erosion tracking can be used to examine the relationship between material erosion and local environment response. For example, the present invention can be used to investigate the modulation stent-based drug elution by blood clots and how this alters arterial drug levels and potential efficacy. Likewise, biomaterial erosion can be followed in both immunodeficient mice and regular mice to study immunological reactions to device erosion.

Figure 4:
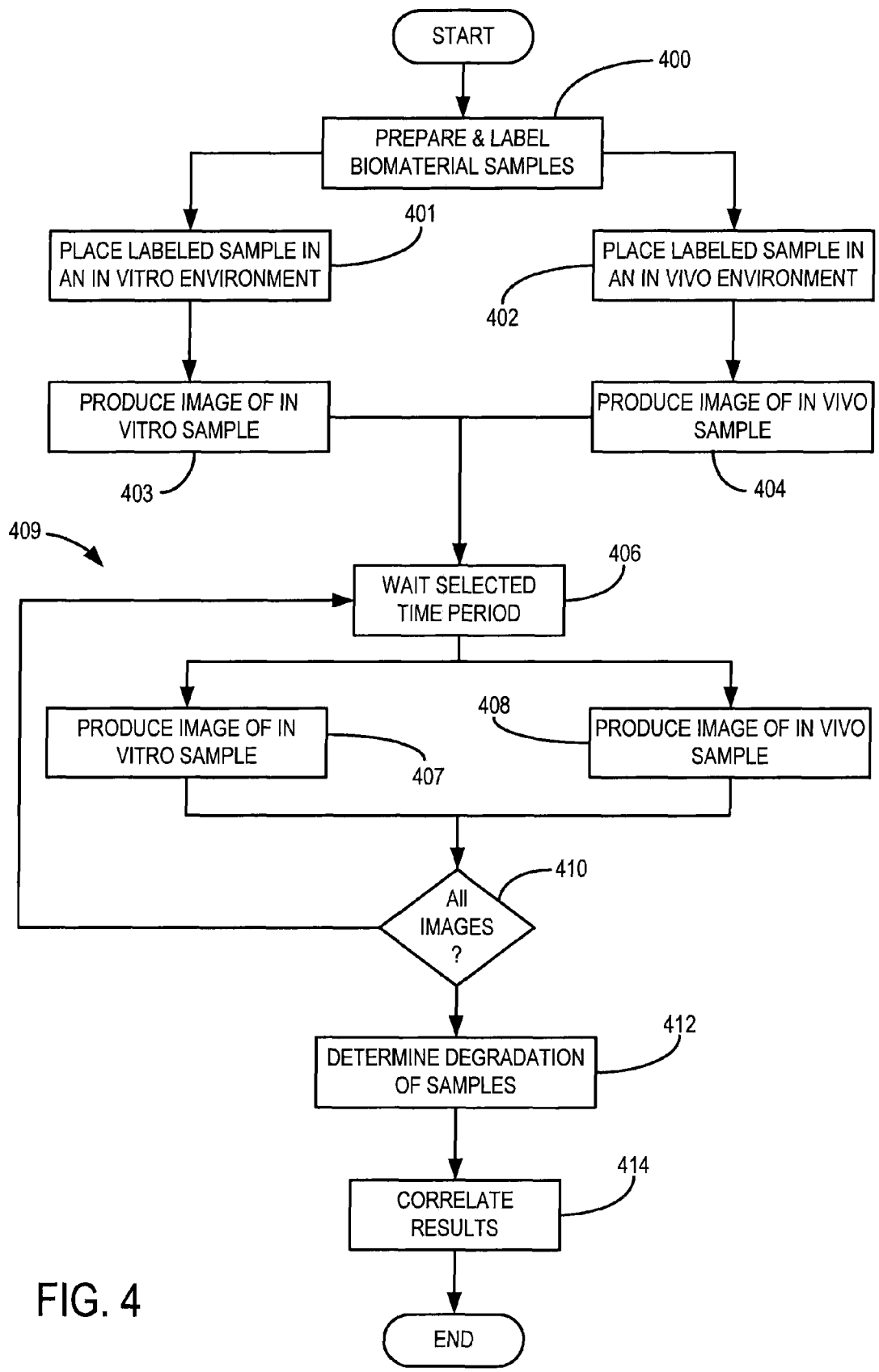
FIG. 4 is a flowchart setting for the steps for creating a model relating biomaterial erosion in the in vivo and in vitro domains in accordance with the present invention.

Referring to FIG. 4, by extending the above-described method, the present invention can be used to generate models relating biomaterial erosion in the in vivo and in vitro domains. As will be described, once this relationship is established, the performance of different biomaterial configurations in vivo can be predicted based on observed in vitro performance. This, for example, enables improved medical device design, since the in vivo performance of a variety of structural and compositional configurations for the medical device can be accurately modeled without the need for in vivo testing. A method for producing a model relating bioerosion the in vitro and in vivo domains begins at process block 300 with the labeling of biomaterial samples. At least two samples of the biomaterial are labeled with a marker and one sample is used for in vitro examination and another is used for in vivo examination. It is contemplated that the marker is a fluorophore attached to the biomaterial sample. For example, the fluorophore may be covalently attached to a polymer-based component of the biomaterial sample.

At process blocks 401 and 402, respectively, the in vitro sample is introduced into an in vitro environment and the in vivo sample is introduced into an in vivo environment. For example, if the biomaterial under study is a polymeric coating for an endovascular stent, the vasculature of a rat, mouse, or pig may be selected as a suitable in vivo environment. Likewise, the in vitro environment is chosen to mimic the in vivo environment as closely as possible. If studying the polymeric coating for the endovascular stent, the in vitro environment may be designed to approximate the pH levels and other physiological conditions commonly found in mammalian vasculature. The in vitro and in vivo samples are imaged at process block 403 and 404, respectively, to produce initial images indicative of sample luminescence. A prescribed period of time is then allowed to expire, as indicated at process block 406. The period of time selected generally depends on the desired clinical application of the candidate biomaterial and on the frequency of measurements desired by a practitioner. For example, if information characterizing the erosion of the biomaterial over the course of several weeks is desired, then the time period selected may be on the order of 12 hours so that images are produced twice per day.

After the selected time period elapses, additional images of the in vitro and in vivo samples are acquired at process blocks 407 and 408, respectively. As indicated generally at 409, additional images can be acquired by cycling through the steps of process block 406-408. The cycle continues until, at decision block 410, it is determined that a sufficient number of images have been acquired. It should be noted that the selected time period between consecutive image acquisitions can change over the course of a scan. For example, longer delays may be used when biomaterial erosion is expected to be stable. At process 412, changes in luminescence between the in vitro and in vivo images acquired at different times are analyzed to determine an in vitro marker decay characteristic and an in vivo marker decay characteristic. At process block 414, these marker decay characteristics are correlated to determine the relationship between biomaterial erosion in vitro and in vivo. This relationship can also be used to investigate the role of medical device ultra structure and composition on in vivo erosion and better inform medical device design and regulatory evaluation. For example, biomaterial bulk properties, such as size, shape, and patterning, can significantly affect biocompatibility, which in turn affects erosion kinetics. For example, the addition of pores to a biomaterial changes its surface patterning and can lead to different interactions with a subject, for example, whether encapsulation will occur, that alter erosion rates. The present invention can therefore be employed to test the effects bulk properties on biomaterial performance. This evaluation can be performed in vivo or predicted from in vitro using a model relating the two domains such as that produced at process block 412.

As mentioned above, present invention can track biomaterial erosion in vivo using bioluminescent markers as well as fluorophores. It is contemplated that the method is performed by detecting light generated by the interaction of systemically administered luciferin and locally produced luciferase. Cells within the biomaterial can be infected with the adeno associated virus (AAV) vector encoding luciferase before transplantation. By administering luciferin to the sample right before imaging, luciferase expression can be quantified in order to non-invasively following cell potency in vivo. For example, an in vivo imaging method utilizing transgenic bioluminescence can be employed, in which developed transgenic mice have localized expression of a bioluminescent enzyme, commonly luciferase. Luciferin is injected to react with the luciferase and create bioluminescence at the site of luciferase expression. The mouse is then imaged after a delay period, for example, 25 minutes, that allows the luciferin-luciferase reaction to produce a detectable level of bioluminescence. After subtracting out background luminescence, the resulting bioluminescence image can be used to track cell survivability, while an accompanying set of fluorescent images can be used to track biomaterial erosion.

The use of fluorescently labeled materials can also be extended to follow not only erosion kinetics, but also mode of degradation. For instance, a material including two polymers can be labeled with different fluorescent markers to determine which material dictates erosion and what bonds are cleaved in the process. Biomaterial composition can then be adjusted based on the determined mode of erosion to provide erosion kinetics best suited to a particular task. Also, by incorporating multiple concomitant tags in drugs or cells and using generating a model to map in vitro performance to the in vivo domain, the present invention can independently track and correlate drug release and material erosion from a polymer drug-eluting scaffold, or the fate of cells and materials within tissue engineered formulations.

Discrepancies between erosion kinetics observed in the two domains may also raise insights regarding other factors controlling erosion. For example, a tissue reaction to a medical device may cause encapsulation that isolates the device from its environment. If encapsulation is the dominant factor affecting material erosion, then it may be determined that in vitro experiments are irrelevant. Alternately, the in vitro environment can be adjusted to reduce discrepancies between in vivo and in vitro erosion rates and provide an improved approximation of in vivo conditions. It is further contemplated that in vivo imaging of fluorescently-labeled biomaterials also enables non-invasive tracking of biomaterial clearance.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for noninvasively imaging erosion of a biomaterial in vivo within a subject, the method comprising the steps of:
   a) preparing an in vivo biomaterial sample by tagging a sample of the biomaterial with a marker that bonds to the biomaterial;
   b) introducing the tagged biomaterial sample to an in vivo environment, wherein the in vivo environment is within the subject;
   c) acquiring imaging data using a luminescence imaging system from the in vivo environment within the subject including the tagged sample of the biomaterial over a selected time period;
   d) reconstructing a series of images from the imaging data using an image processor, each image characterizing a luminescent property of the in vivo biomaterial sample at a given time in the selected time period; and
   e) determining, from the images, changes in the luminescent property of the biomaterial sample over the selected time period;
   f) determining an in vivo marker characteristic based on the changes in the luminescent property of the biomaterial sample, the in vivo marker characteristic indicative of the erosion of the biomaterial in vivo.

2. The method as recited in claim 1 wherein the in vivo erosion is characteristic of the erosion rate.

3. The method as recited in claim 1 wherein the marker is a fluorophore and the luminescent property of the biomaterial is fluorescence.

4. The method as recited in claim 1 further comprising step g) relating the marker characteristic to viability of cells embedded within the in vivo biomaterial sample.

5. The method as recited in claim 4 wherein step a) includes labeling cells within the biomaterial with a bioluminescent marker and step g) includes generating a bioluminescent marker characteristic indicative of cell viability in the in vivo biomaterial sample and further comprising h) comparing the bioluminescent marker characteristic to the in vivo marker characteristic.

6. The method as recited in claim 5 wherein the marker labeling the cells within the biomaterial is luciferase.

7. The method as recited in claim 1 further comprising g) relating the in vivo marker characteristic to drug release from the in vivo biomaterial sample.

8. The method as recited in claim 7 wherein step a) includes labeling a drug within the biomaterial with a luminescent marker and step g) includes generating a drug release characteristic by analyzing changes in the luminescent property of the biomaterial sample between the acquired images and further comprising h) comparing the drug release characteristic to the in vivo marker characteristic.

9. The method as recited in claim 1 further comprising repeating steps a) through d) using biomaterial samples with varying bulk material properties and wherein step f) includes characterizing changes to biomaterial bulk properties to biomaterial degradation and erosion.

10. The method as recited in claim 1 wherein step:
   a) includes preparing an in vitro biomaterial sample by tagging a sample of the biomaterial with a marker that bonds to the biomaterial and introducing the tagged biomaterial sample to an in vitro environment;
   e) includes characterizing a luminescent property of the in vitro biomaterial sample at a given time; and
   f) includes generating an in vitro marker characteristic indicative of the erosion of the biomaterial in vitro by analyzing changes in the luminescent property of the biomaterial sample between the acquired images.

11. The method as recited in claim 10 further comprising repeating steps a) through d) while changing the in vitro environment in order to reduce differences between in vitro and in vivo marker characteristics and determine in vitro environment changes that better mimic the in vivo environment.

12. The method as recited in claim 10 further comprising comparing the in vitro and in vivo marker characteristics to produce a model relating degradation and erosion of the biomaterials in the in vitro domain to degradation and erosion of the biomaterial in the in vivo domain.

13. The method as recited in claim 12 wherein the model is employed to predict changes in performance of the biomaterial in vivo based on observations of the biomaterial in vitro.

14. The method as recited in claim 13 wherein the model is employed to predict how changes in bulk properties of the biomaterial affect biomaterial degradation in vivo.

15. The method as recited in claim 1 wherein step a) includes labeling the sample of the biomaterial with a plurality of luminescent markers that each attach to a specific component of the biomaterial sample, and step f) includes determining a plurality of marker characteristics, each indicative of the degradation and erosion of the component biomaterial to which they are attached.

16. The method as recited in claim 15 further comprising determining a mode of biomaterial degradation via comparison of the plurality of marker characteristics.

* * * * *